US011596771B2

(12) United States Patent
Torrance et al.

(10) Patent No.: US 11,596,771 B2
(45) Date of Patent: Mar. 7, 2023

(54) MODULAR PRE-LOADED MEDICAL IMPLANTS AND DELIVERY SYSTEMS

(71) Applicant: Cardiac Dimensions Pty. Ltd., Kirkland, WA (US)

(72) Inventors: Casey Torrance, Snohomish, WA (US); Matt Winter, Seattle, WA (US); Timothy Johnson, Kent, WA (US); Jared Salstrom, Lake Stevens, WA (US)

(73) Assignee: Cardiac Dimensions Pty. Ltd., Kirkland, WA (US)

( * ) Notice: Subject to any disclaimer, the term of this patent is extended or adjusted under 35 U.S.C. 154(b) by 0 days.

(21) Appl. No.: 17/643,689

(22) Filed: Dec. 10, 2021

(65) Prior Publication Data

US 2022/0184344 A1 Jun. 16, 2022

Related U.S. Application Data

(60) Provisional application No. 63/125,260, filed on Dec. 14, 2020.

(51) Int. Cl.
*A61M 25/01* (2006.01)
*A61B 17/12* (2006.01)
*A61M 25/00* (2006.01)

(52) U.S. Cl.
CPC ..... *A61M 25/0136* (2013.01); *A61B 17/1214* (2013.01); *A61M 25/002* (2013.01); *A61B 2017/12054* (2013.01)

(58) Field of Classification Search
CPC ............ A61M 25/0136; A61M 25/002; A61B 17/1214; A61B 2017/12054; A61B 50/20; A61B 50/33; A61F 2/95; A61F 2/9517; A61F 2/2451; A61F 2/2466; A61F 2/0095
See application file for complete search history.

(56) References Cited

U.S. PATENT DOCUMENTS

| 3,620,212 | A | 11/1971 | Fannon, Jr. et al. |
| 3,786,806 | A | 1/1974 | Johnson et al. |
| 3,890,977 | A | 6/1975 | Wilson |
| 3,974,526 | A | 8/1976 | Dardik et al. |
| 3,995,623 | A | 12/1976 | Blake et al. |

(Continued)

FOREIGN PATENT DOCUMENTS

| EP | 0893133 A1 | 1/1999 |
| EP | 0903110 A1 | 3/1999 |

(Continued)

OTHER PUBLICATIONS

El-Maasarany et al.; The coronary sinus conduit function: Anatomical study (relationship to adjacent structures); http://europace.oxfordjournals.org/cge/content/full/7/5/475. (accessed Sep. 9, 2008).

(Continued)

*Primary Examiner* — Robert A Lynch
*Assistant Examiner* — Mikail A Mannan
(74) *Attorney, Agent, or Firm* — Shay Glenn LLP; Thomas M. Zlogar

(57) ABSTRACT

Modular pre-loaded implant subassemblies that can be packaged separately from a handle, which allows using any one of a plurality of separately packaged modular pre-loaded implants with a common handle.

20 Claims, 12 Drawing Sheets

(56) References Cited

U.S. PATENT DOCUMENTS

| | | |
|---|---|---|
| 4,055,861 A | 11/1977 | Carpentier et al. |
| 4,164,046 A | 8/1979 | Cooley |
| 4,485,816 A | 12/1984 | Krumme |
| 4,550,870 A | 11/1985 | Krumme et al. |
| 4,588,395 A | 5/1986 | Lemelson |
| 4,830,023 A | 5/1989 | de Toledo et al. |
| 5,061,277 A | 10/1991 | Carpentier et al. |
| 5,099,838 A | 3/1992 | Bardy |
| 5,104,404 A | 4/1992 | Wolff |
| 5,197,978 A | 3/1993 | Hess |
| 5,250,071 A | 10/1993 | Palermo |
| 5,261,916 A | 11/1993 | Engelson |
| 5,265,601 A | 11/1993 | Mehra |
| 5,344,426 A | 9/1994 | Lau et al. |
| 5,350,420 A | 9/1994 | Cosgrove et al. |
| 5,411,549 A | 5/1995 | Peters |
| 5,433,727 A | 7/1995 | Sideris |
| 5,441,515 A | 8/1995 | Khosravi et al. |
| 5,449,373 A | 9/1995 | Pinchasik et al. |
| 5,454,365 A | 10/1995 | Bonutti |
| 5,458,615 A | 10/1995 | Klemm et al. |
| 5,474,557 A | 12/1995 | Mai |
| 5,507,295 A | 4/1996 | Skidmore |
| 5,507,802 A | 4/1996 | Imran |
| 5,514,161 A | 5/1996 | Limousin |
| 5,554,177 A | 9/1996 | Kieval et al. |
| 5,562,698 A | 10/1996 | Parker |
| 5,575,818 A | 11/1996 | Pinchuk |
| 5,584,867 A | 12/1996 | Limousin et al. |
| 5,601,600 A | 2/1997 | Ton |
| 5,609,605 A | 3/1997 | Marshall et al. |
| 5,617,854 A | 4/1997 | Munsif |
| 5,662,703 A | 9/1997 | Yurek et al. |
| 5,676,671 A | 10/1997 | Inoue |
| 5,733,325 A | 3/1998 | Robinson et al. |
| 5,733,328 A | 3/1998 | Fordenbacher |
| 5,741,297 A | 4/1998 | Simon |
| 5,752,969 A | 5/1998 | Cunci et al. |
| 5,800,519 A | 9/1998 | Sandock |
| 5,824,071 A | 10/1998 | Nelson et al. |
| 5,836,882 A | 11/1998 | Frazin |
| 5,871,501 A | 2/1999 | Leschinsky et al. |
| 5,891,193 A | 4/1999 | Robinson et al. |
| 5,895,391 A | 4/1999 | Farnholtz |
| 5,899,882 A | 5/1999 | Waksman et al. |
| 5,908,404 A | 6/1999 | Elliot |
| 5,928,258 A | 7/1999 | Khan et al. |
| 5,935,161 A | 8/1999 | Robinson et al. |
| 5,954,761 A | 9/1999 | Machek et al. |
| 5,961,545 A | 10/1999 | Lentz et al. |
| 5,978,705 A | 11/1999 | KenKnight et al. |
| 5,984,944 A | 11/1999 | Forber |
| 6,001,118 A | 12/1999 | Daniel et al. |
| 6,007,519 A | 12/1999 | Rosselli |
| 6,015,402 A | 1/2000 | Sahota |
| 6,022,371 A | 2/2000 | Killion |
| 6,027,517 A | 2/2000 | Crocker et al. |
| 6,045,497 A | 4/2000 | Schweich, Jr. et al. |
| 6,053,900 A | 4/2000 | Brown et al. |
| 6,056,775 A | 5/2000 | Borghi et al. |
| 6,077,295 A | 6/2000 | Limon et al. |
| 6,077,297 A | 6/2000 | Robinson et al. |
| 6,080,182 A | 6/2000 | Shaw et al. |
| 6,086,611 A | 7/2000 | Duffy et al. |
| 6,096,064 A | 8/2000 | Routh |
| 6,099,549 A | 8/2000 | Bosma et al. |
| 6,099,552 A | 8/2000 | Adams |
| 6,129,755 A | 10/2000 | Mathis et al. |
| 6,159,220 A | 12/2000 | Gobron et al. |
| 6,162,168 A | 12/2000 | Schweich, Jr. et al. |
| 6,171,320 B1 | 1/2001 | Monassevitch |
| 6,183,512 B1 | 2/2001 | Howanec et al. |
| 6,190,406 B1 | 2/2001 | Duerig et al. |
| 6,200,336 B1 | 3/2001 | Pavcnik et al. |
| 6,210,432 B1 | 4/2001 | Solem et al. |
| 6,228,098 B1 | 5/2001 | Kayan et al. |
| 6,241,757 B1 | 6/2001 | An et al. |
| 6,254,628 B1 | 7/2001 | Wallace et al. |
| 6,267,783 B1 | 7/2001 | Letendre et al. |
| 6,275,730 B1 | 8/2001 | KenKnight et al. |
| 6,306,141 B1 | 10/2001 | Jervis |
| 6,312,446 B1 | 11/2001 | Huebsch et al. |
| 6,334,864 B1 | 1/2002 | Amplatz et al. |
| 6,342,067 B1 | 1/2002 | Mathis et al. |
| 6,345,198 B1 | 2/2002 | Mouchawar et al. |
| 6,352,553 B1 | 3/2002 | van der Burg et al. |
| 6,352,561 B1 | 3/2002 | Leopold et al. |
| 6,358,195 B1 | 3/2002 | Green et al. |
| 6,368,345 B1 | 4/2002 | Dehdashtian et al. |
| 6,395,017 B1 | 5/2002 | Dwyer et al. |
| 6,402,781 B1 | 6/2002 | Langberg et al. |
| 6,409,750 B1 | 6/2002 | Hyodoh et al. |
| 6,419,696 B1 | 7/2002 | Ortiz et al. |
| 6,442,427 B1 | 8/2002 | Boute et al. |
| 6,464,720 B2 | 10/2002 | Boatman et al. |
| 6,478,776 B1 | 11/2002 | Rosenman et al. |
| 6,503,271 B2 | 1/2003 | Duerig et al. |
| 6,537,314 B2 | 3/2003 | Langberg et al. |
| 6,556,873 B1 | 4/2003 | Smits |
| 6,562,066 B1 | 5/2003 | Martin |
| 6,562,067 B2 | 5/2003 | Mathis |
| 6,569,198 B1 | 5/2003 | Wilson et al. |
| 6,589,208 B2 | 7/2003 | Ewers et al. |
| 6,599,314 B2 | 7/2003 | Mathis et al. |
| 6,602,288 B1 | 8/2003 | Cosgrove et al. |
| 6,602,289 B1 | 8/2003 | Colvin et al. |
| 6,623,521 B2 | 9/2003 | Steinke et al. |
| 6,626,899 B2 | 9/2003 | Houser et al. |
| 6,629,534 B1 | 10/2003 | St. Goar et al. |
| 6,629,994 B2 | 10/2003 | Gomez et al. |
| 6,643,546 B2 | 11/2003 | Mathis et al. |
| 6,648,881 B2 | 11/2003 | KenKnight et al. |
| 6,652,538 B2 | 11/2003 | Kayan et al. |
| 6,652,571 B1 | 11/2003 | White et al. |
| 6,656,221 B2 | 12/2003 | Taylor et al. |
| 6,676,702 B2 | 1/2004 | Mathis |
| 6,689,164 B1 | 2/2004 | Seguin |
| 6,709,425 B2 | 3/2004 | Gambale et al. |
| 6,716,158 B2 | 4/2004 | Raman et al. |
| 6,718,985 B2 | 4/2004 | Hlavka et al. |
| 6,721,598 B1 | 4/2004 | Helland et al. |
| 6,723,038 B1 | 4/2004 | Schroeder et al. |
| 6,733,521 B2 | 5/2004 | Chobotov et al. |
| 6,743,219 B1 | 6/2004 | Dwyer et al. |
| 6,764,510 B2 | 7/2004 | Vidlund et al. |
| 6,773,446 B1 | 8/2004 | Dwyer et al. |
| 6,776,784 B2 | 8/2004 | Ginn |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,800,090 B2 | 10/2004 | Alferness et al. |
| 6,805,128 B1 | 10/2004 | Pless et al. |
| 6,810,882 B2 | 11/2004 | Langberg et al. |
| 6,814,752 B1 | 11/2004 | Chuter |
| 6,821,297 B2 | 11/2004 | Snyders |
| 6,824,562 B2 | 11/2004 | Mathis et al. |
| 6,827,690 B2 | 12/2004 | Bardy |
| 6,881,220 B2 | 4/2005 | Edwin et al. |
| 6,890,353 B2 | 5/2005 | Cohn et al. |
| 6,899,734 B2 | 5/2005 | Castro et al. |
| 6,908,478 B2 | 6/2005 | Alferness et al. |
| 6,908,482 B2 | 6/2005 | McCarthy et al. |
| 6,926,690 B2 | 8/2005 | Renati |
| 6,935,404 B2 | 8/2005 | Duerig et al. |
| 6,949,122 B2 | 9/2005 | Adams et al. |
| 6,955,689 B2 | 10/2005 | Ryan et al. |
| 6,960,229 B2 | 11/2005 | Mathis et al. |
| 6,964,683 B2 | 11/2005 | Kowalsky et al. |
| 6,966,926 B2 | 11/2005 | Mathis |
| 6,976,995 B2 | 12/2005 | Mathis et al. |
| 7,004,958 B2 | 2/2006 | Adams et al. |
| 7,087,064 B1 | 8/2006 | Hyde |
| 7,128,073 B1 | 10/2006 | van der Burg et al. |
| 7,152,605 B2 | 12/2006 | Khairkhahan et al. |

(56) References Cited

U.S. PATENT DOCUMENTS

| | | |
|---|---|---|
| 7,175,653 B2 | 2/2007 | Gaber |
| 7,179,282 B2 | 2/2007 | Alferness et al. |
| 7,270,676 B2 | 9/2007 | Alferness et al. |
| 7,276,078 B2 | 10/2007 | Spenser et al. |
| 7,309,354 B2 | 12/2007 | Mathis et al. |
| 7,311,729 B2 | 12/2007 | Mathis et al. |
| 7,316,708 B2 | 1/2008 | Gordon et al. |
| 7,364,588 B2 | 4/2008 | Mathis et al. |
| 7,452,375 B2 | 11/2008 | Mathis et al. |
| 7,503,931 B2 | 3/2009 | Kowalsky et al. |
| 7,591,826 B2 | 9/2009 | Alferness et al. |
| 7,608,102 B2 | 10/2009 | Adams et al. |
| 7,635,387 B2 | 12/2009 | Reuter et al. |
| 7,637,946 B2 | 12/2009 | Solem et al. |
| 7,674,287 B2 | 3/2010 | Alferness et al. |
| 7,758,639 B2 | 7/2010 | Mathis |
| 7,814,635 B2 | 10/2010 | Gordon |
| 7,828,841 B2 | 11/2010 | Mathis et al. |
| 7,828,842 B2 | 11/2010 | Nieminen et al. |
| 7,828,843 B2 | 11/2010 | Alferness et al. |
| 7,837,728 B2 | 11/2010 | Nieminen et al. |
| 7,837,729 B2 | 11/2010 | Gordon et al. |
| 7,887,582 B2 | 2/2011 | Mathis et al. |
| 7,955,384 B2 | 6/2011 | Rafiee et al. |
| 8,006,594 B2 | 8/2011 | Hayner et al. |
| 8,062,358 B2 | 11/2011 | Mathis et al. |
| 8,075,608 B2 | 12/2011 | Gordon et al. |
| 8,172,898 B2 | 5/2012 | Alferness et al. |
| 8,182,529 B2 | 5/2012 | Gordon et al. |
| 8,250,960 B2 | 8/2012 | Hayner et al. |
| 8,366,720 B2 | 2/2013 | Mitelberg et al. |
| 8,439,971 B2 | 5/2013 | Reuter et al. |
| 8,679,174 B2 | 3/2014 | Ottma et al. |
| 8,795,356 B2 | 8/2014 | Quadri et al. |
| 8,974,525 B2 | 3/2015 | Nieminen et al. |
| 9,039,757 B2 | 5/2015 | McLean et al. |
| 9,084,676 B2 | 7/2015 | Chau et al. |
| 9,320,600 B2 | 4/2016 | Nieminen et al. |
| 9,370,418 B2 | 6/2016 | Pintor et al. |
| 9,408,695 B2 | 8/2016 | Mathis et al. |
| 9,474,608 B2 | 10/2016 | Mathis et al. |
| 9,526,616 B2 | 12/2016 | Nieminen et al. |
| 9,597,186 B2 | 3/2017 | Nieminen et al. |
| 9,827,098 B2 | 11/2017 | Mathis et al. |
| 9,827,099 B2 | 11/2017 | Mathis et al. |
| 9,827,100 B2 | 11/2017 | Mathis et al. |
| 9,956,076 B2 | 5/2018 | Mathis et al. |
| 9,956,077 B2 | 5/2018 | Nieminen et al. |
| 10,052,205 B2 | 8/2018 | Mathis et al. |
| 10,166,102 B2 | 1/2019 | Nieminen et al. |
| 10,327,900 B2 | 6/2019 | Mathis et al. |
| 10,449,048 B2 | 10/2019 | Nieminen et al. |
| 10,456,257 B2 | 10/2019 | Mathis et al. |
| 10,456,259 B2 | 10/2019 | Mathis et al. |
| 11,033,257 B2 | 6/2021 | Nieminen et al. |
| 11,109,971 B2 | 9/2021 | Nieminen et al. |
| 2001/0018611 A1 | 8/2001 | Solem et al. |
| 2001/0041899 A1 | 11/2001 | Foster |
| 2001/0044568 A1 | 11/2001 | Langberg et al. |
| 2001/0049558 A1 | 12/2001 | Liddicoat et al. |
| 2002/0010507 A1 | 1/2002 | Ehr et al. |
| 2002/0016628 A1 | 2/2002 | Langberg et al. |
| 2002/0042621 A1 | 4/2002 | Liddicoat et al. |
| 2002/0042651 A1 | 4/2002 | Liddicoat et al. |
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0095167 A1 | 7/2002 | Liddicoat et al. |
| 2002/0138044 A1 | 9/2002 | Streeter et al. |
| 2002/0151961 A1 | 10/2002 | Lashinski et al. |
| 2002/0156526 A1 | 10/2002 | Hlavka et al. |
| 2002/0161377 A1 | 10/2002 | Rabkin et al. |
| 2002/0161393 A1 | 10/2002 | Demond et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2002/0193827 A1 | 12/2002 | McGuckin et al. |
| 2003/0018358 A1 | 1/2003 | Saadat |
| 2003/0040771 A1 | 2/2003 | Hyodoh et al. |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0083613 A1 | 5/2003 | Schaer |
| 2003/0088305 A1 | 5/2003 | Van Schie et al. |
| 2003/0093148 A1 | 5/2003 | Bolling et al. |
| 2003/0130730 A1 | 7/2003 | Cohn et al. |
| 2003/0135267 A1 | 7/2003 | Solem et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0098116 A1 | 5/2004 | Callas et al. |
| 2004/0102839 A1 | 5/2004 | Cohn et al. |
| 2004/0102840 A1 | 5/2004 | Solem et al. |
| 2004/0127982 A1 | 7/2004 | Machold et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153147 A1 | 8/2004 | Mathis |
| 2004/0158321 A1 | 8/2004 | Reuter et al. |
| 2004/0172046 A1 | 9/2004 | Hlavka et al. |
| 2004/0176840 A1 | 9/2004 | Langberg |
| 2004/0193191 A1 | 9/2004 | Starksen et al. |
| 2004/0193260 A1 | 9/2004 | Alferness et al. |
| 2004/0220654 A1 | 11/2004 | Mathis et al. |
| 2004/0220657 A1 | 11/2004 | Nieminen et al. |
| 2004/0243227 A1 | 12/2004 | Starksen et al. |
| 2004/0260342 A1 | 12/2004 | Vargas et al. |
| 2004/0260384 A1 | 12/2004 | Allen |
| 2005/0004667 A1 | 1/2005 | Swinford et al. |
| 2005/0027351 A1 | 2/2005 | Reuter et al. |
| 2005/0033419 A1 | 2/2005 | Alferness et al. |
| 2005/0060030 A1 | 3/2005 | Lashinski et al. |
| 2005/0085903 A1 | 4/2005 | Lau |
| 2005/0096666 A1* | 5/2005 | Gordon ............ A61F 2/2451 623/1.11 |
| 2005/0096740 A1 | 5/2005 | Langberg et al. |
| 2005/0107810 A1 | 5/2005 | Morales et al. |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0149182 A1 | 7/2005 | Alferness et al. |
| 2005/0177228 A1 | 8/2005 | Solem et al. |
| 2005/0197692 A1 | 9/2005 | Pai et al. |
| 2005/0197693 A1 | 9/2005 | Pal et al. |
| 2005/0197694 A1 | 9/2005 | Pai et al. |
| 2005/0209690 A1 | 9/2005 | Mathis et al. |
| 2005/0216077 A1 | 9/2005 | Mathis et al. |
| 2005/0222678 A1 | 10/2005 | Lashinski et al. |
| 2005/0261704 A1 | 11/2005 | Mathis |
| 2005/0272969 A1 | 12/2005 | Alferness et al. |
| 2006/0030882 A1 | 2/2006 | Adams et al. |
| 2006/0041305 A1 | 2/2006 | Lauterjung |
| 2006/0116758 A1 | 6/2006 | Swinford et al. |
| 2006/0142854 A1 | 6/2006 | Alferness et al. |
| 2006/0161169 A1 | 7/2006 | Nieminen et al. |
| 2006/0167544 A1 | 7/2006 | Nieminen et al. |
| 2006/0271174 A1 | 11/2006 | Nieminen et al. |
| 2007/0027533 A1 | 2/2007 | Douk |
| 2007/0066879 A1 | 3/2007 | Mathis et al. |
| 2007/0073391 A1 | 3/2007 | Bourang et al. |
| 2007/0173926 A1 | 7/2007 | Bobo, Jr. et al. |
| 2007/0239270 A1 | 10/2007 | Mathis et al. |
| 2008/0015407 A1 | 1/2008 | Mathis et al. |
| 2008/0015679 A1 | 1/2008 | Mathis et al. |
| 2008/0015680 A1 | 1/2008 | Mathis et al. |
| 2008/0071364 A1 | 3/2008 | Kaye et al. |
| 2008/0221673 A1 | 9/2008 | Bobo et al. |
| 2010/0030330 A1 | 2/2010 | Bobo et al. |
| 2010/0280602 A1 | 11/2010 | Mathis |

(56) References Cited

U.S. PATENT DOCUMENTS

| | | |
|---|---|---|
| 2011/0066234 A1 | 3/2011 | Gordon et al. |
| 2011/0106117 A1 | 5/2011 | Mathis et al. |
| 2011/0257563 A1 | 10/2011 | Thapliyal et al. |
| 2012/0123532 A1 | 5/2012 | Mathis |
| 2012/0197389 A1 | 8/2012 | Alferness et al. |
| 2014/0275757 A1 | 9/2014 | Goodwin et al. |
| 2017/0165058 A1 | 6/2017 | Rothstein et al. |
| 2017/0189185 A1 | 7/2017 | Nieminen et al. |
| 2018/0078365 A1 | 3/2018 | Zhang et al. |
| 2018/0256330 A1 | 9/2018 | Wypych |
| 2019/0336290 A1 | 11/2019 | Mathis et al. |
| 2019/0350708 A1 | 11/2019 | Mathis et al. |
| 2019/0365537 A1 | 12/2019 | Wypych |
| 2020/0008943 A1 | 1/2020 | Mathis et al. |
| 2020/0253732 A1 | 8/2020 | Nieminen et al. |
| 2021/0298732 A1 | 9/2021 | Nieminen et al. |
| 2021/0330460 A1 | 10/2021 | Mathis et al. |
| 2021/0393403 A1 | 12/2021 | Nieminen et al. |

FOREIGN PATENT DOCUMENTS

| | | |
|---|---|---|
| EP | 0968688 A1 | 1/2000 |
| EP | 1050274 A1 | 11/2000 |
| EP | 1095634 A2 | 5/2001 |
| EP | 1177779 A2 | 2/2002 |
| EP | 2181670 A2 | 5/2010 |
| GB | 0741604 | 12/1955 |
| JP | 2754067 | 3/1998 |
| JP | 2000-308652 | 11/2000 |
| JP | 2001-503291 | 3/2001 |
| JP | 2003-503101 | 1/2003 |
| JP | 2003-521310 | 7/2003 |
| SE | 9902455 | 12/2000 |
| WO | WO98/56435 A1 | 12/1998 |
| WO | WO00/44313 A1 | 8/2000 |
| WO | WO00/60995 A2 | 10/2000 |
| WO | WO00/74603 A1 | 12/2000 |
| WO | WO01/00111 A1 | 1/2001 |
| WO | WO01/19292 A1 | 3/2001 |
| WO | WO01/50985 A1 | 7/2001 |
| WO | WO01/54618 A1 | 8/2001 |
| WO | WO01/87180 A2 | 11/2001 |
| WO | WO02/00099 A2 | 1/2002 |
| WO | WO02/01999 A2 | 1/2002 |
| WO | WO02/05888 A1 | 1/2002 |
| WO | WO02/19951 A1 | 3/2002 |
| WO | WO02/34118 A2 | 5/2002 |
| WO | WO02/47539 A2 | 6/2002 |
| WO | WO02/053206 A2 | 7/2002 |
| WO | WO02/060352 A1 | 8/2002 |
| WO | WO02/062263 A2 | 8/2002 |
| WO | WO02/062270 A1 | 8/2002 |
| WO | WO02/062408 A2 | 8/2002 |
| WO | WO02/076284 A2 | 10/2002 |
| WO | WO02/078576 A2 | 10/2002 |
| WO | WO02/096275 A2 | 12/2002 |
| WO | WO03/015611 A2 | 2/2003 |
| WO | WO03/037171 A2 | 5/2003 |
| WO | WO03/049647 A1 | 6/2003 |
| WO | WO03/049648 A2 | 6/2003 |
| WO | WO03/055417 A1 | 7/2003 |
| WO | WO03/059198 A2 | 7/2003 |
| WO | WO03/063735 A2 | 8/2003 |
| WO | WO2004/045463 A2 | 6/2004 |
| WO | WO2004/084746 A2 | 10/2004 |
| WO | WO2005/046531 A2 | 5/2005 |
| WO | WO2005/058206 A1 | 6/2005 |
| WO | WO2006/002492 A1 | 1/2006 |

OTHER PUBLICATIONS

Gray, H. Anatomy of the Human Body. The Systemic Veins. Philadelphia: Lea & Febiger, 1918; Bartleby.com. 2000. Available at www.bartleby.com/107/. Accessed Jun. 7, 2006.

Halees; An additional maneuver to repair mitral paravalvular leak; European Journal of Cardio-Thoracic Surgery; 39(3); pp. 410-411; Mar. 2011.

Heartsite.com. Echocardiogram, 1999; p. 1-4. A.S.M. Systems Inc. Available at: http://www.heartsite.com/html/echocardiogram.html. Accessed Jul. 1, 2005.

Papageorgiou, P., et al. Coronary Sinus Pacing Prevents induction of Atrial Fibrillation. Circulation. Sep. 16, 1997; 96(6): 1893-1898.

Pelton et al. Medical uses of nitinol; Material Science Forum; vols. 327-328; pp. 63-70; 2000 (held in Kanazawa, Japan, May 1999).

Pijls et al.; Measurement of fractional flow reserve to assess the functional severity of coronary-artery stenoses; The New England J. of Med.; vol. 334; No. 26; pp. 1703-1708; Jun. 27, 1996.

Pai, Suresh; U.S. Appl. No. 60/329,694 entitled "Percutaneous cardiac support structures and deployment means," filed Oct. 16, 2001.

Webb, et al. Percutaneous transvenous mitral annuloplasty initial human experience with device implantation in the coronary sinus. Circulation. Feb. 14, 2006; 851-855.

Yamanouchi, et al.; Activation Mapping from the coronary sinus may be limited by anatomic variations; vol. 21 pp. 2522-2526; Nov. 1998.

Nieminen et al.; U.S. Appl. No. 17/655,974 entitled "Mitral valve annuloplasty device with twisted anchor," filed Mar. 22, 2022.

* cited by examiner

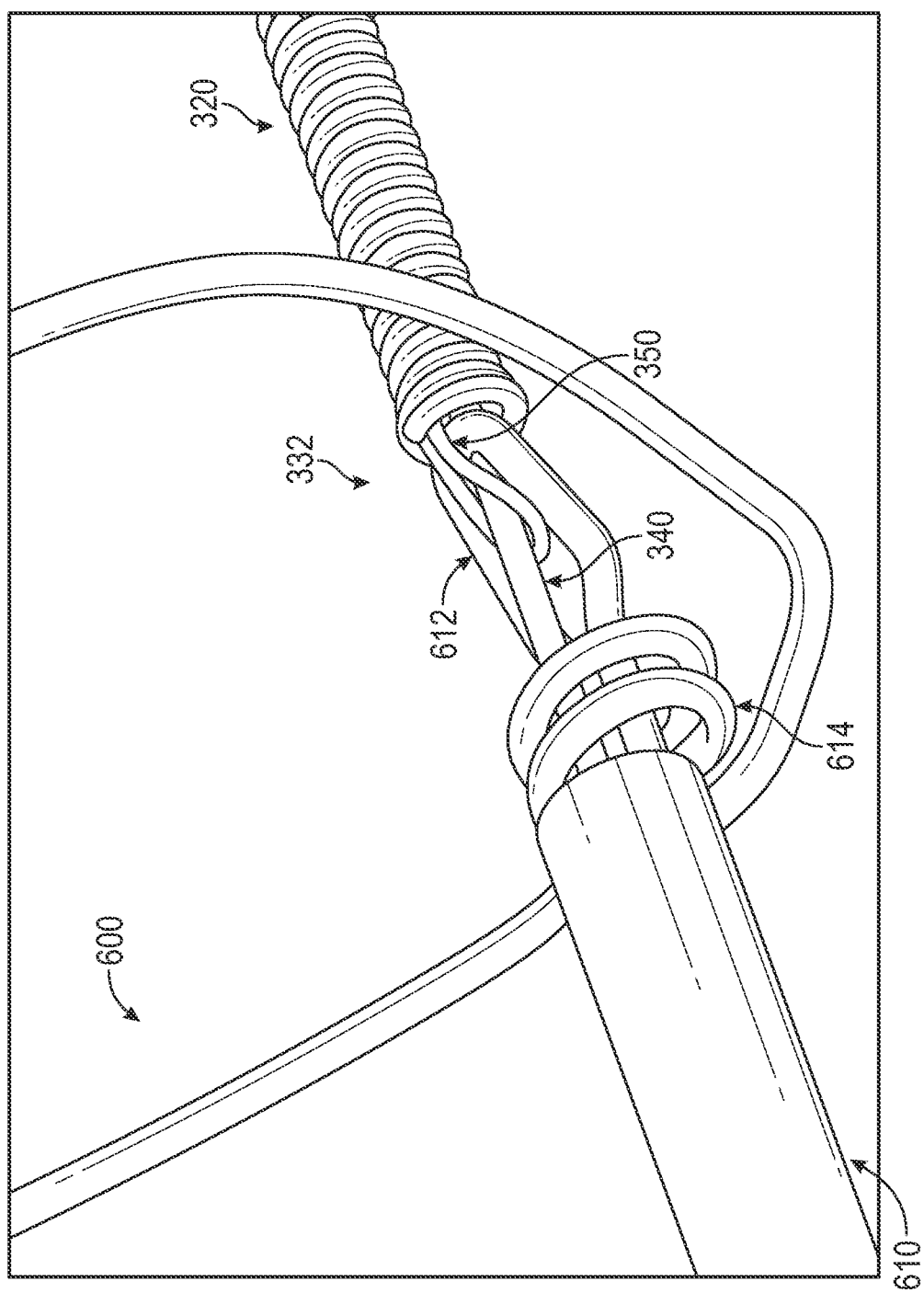

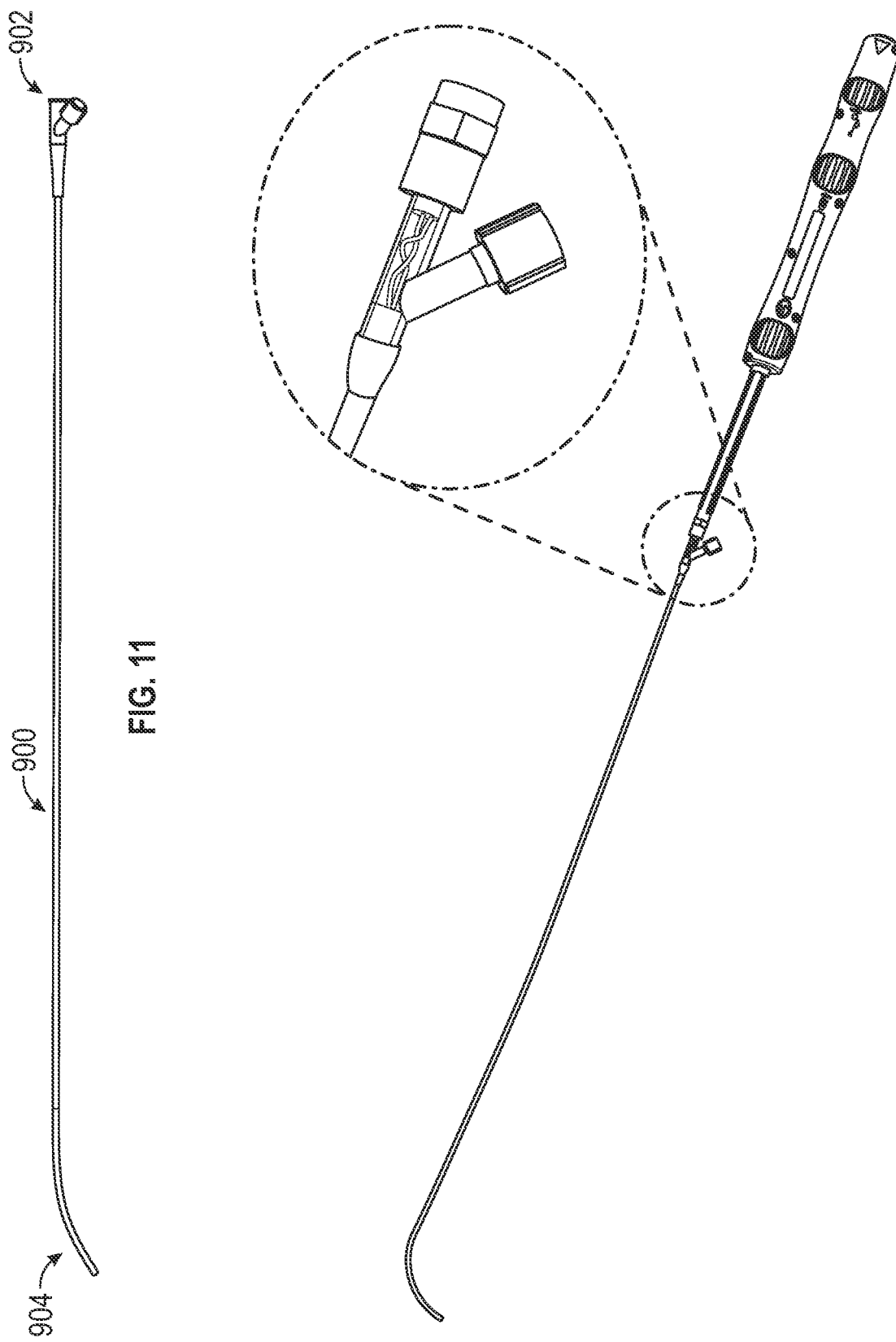

MODULAR PRE-LOADED MEDICAL IMPLANTS AND DELIVERY SYSTEMS

CROSS REFERENCE TO RELATED APPLICATIONS

This application claims the benefit of priority to U.S. Provisional Application No. 63/125,260, filed Dec. 14, 2020, the entire disclosure of which is incorporated by reference herein for all purposes.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Many implantable medical devices are adapted to be delivered to a target location within a patient with a delivery system. Delivery systems commonly include an external handle assembly that facilitates one or more aspects of the implant delivery and implantation. Some medical devices may be coupled with the delivery system during manufacturing and packaged with the delivery system. During the medical procedure, the implants may be decoupled and detached from the delivery system to fully implant the medical device.

For a variety of reasons, some medical procedures may require having more than one implant that may be prepared and ready to be implanted if needed. For example, if an implant comes out of the packaging damaged or is unsafe, a different implant may need to be removed from its package and used instead. Additionally, some medical procedures may require having a plurality of implants ready for use, each of which may have at least one physical characteristic different from at least one of the other available implants. For example, some procedures may deliver an implant to an anatomical location for which there is some degree of patient-to-patient variability in size and/or configuration. The particulars of the patient's anatomy may not be known or confirmed until the procedure begins, which may be determined using one or more imaging techniques (e.g., x-ray, fluoroscopy, etc.). Implants with different size(s) and/or configurations must be available if needed depending on the particular patient anatomy. The configuration of the implant and/or the manner in which it is used may also impact how many implants must be ready and available for implantation for any particular procedure. For example, the number of and configuration of individual implant components may require that several implants be ready, each with different components with different sizes. Additionally, a variety of possible sizes and/or configurations for one or more individual components may require a matrix of implant possibilities with components of different sizes and/or configuration, all of which must be shipped for a particular procedure and be ready for use during the procedure. Depending on the procedure, several implants may be needed and available for selection, such as more than five, or more than ten, or in some cases more than fifteen or even more.

When a delivery system is coupled to an implant during manufacture and packaged this way, each package (e.g., box) will have a full system including a potentially bulky handle in addition to the implant. For medical procedures that require several or many implants to be available for use, many packages, each of which includes a delivery system coupled to the implant, may be needed in close proximity to the medical personnel.

In addition, some medical procedures are performed in a cardiac catheterization lab ("cath lab"), in which there may not be a great deal of available space for medical supplies such as packaging and boxes in which the implants and delivery systems are stored. In some cases, the delivery system and implant packaging may be of such a large number that they must be positioned outside the cath lab, requiring medical personnel to leave the cath lab and procure the desired implant during the procedure.

Some medical procedures may benefit from having packaging and assembly solutions that reduce the amount of packaging needed for the procedure.

SUMMARY OF THE DISCLOSURE

One aspect of the disclosure is an implant subassembly adapted to be coupled to a handle subassembly during a medical procedure for implanting an implant within a patient. The implant subassembly may comprise a cartridge and an implant disposed in a collapsed state within the cartridge, the implant having an implant proximal end, an elongate flexible tubular member with a distal end adjacent the implant proximal end, and an implant coupling mechanism including first and second coupling members that extend through the flexible tubular member, the first and second coupling members coupled to the implant proximal end in a first state and positioned and configured to release the implant proximal end in a second state.

In this aspect, the flexible tubular member may comprise a helically coiled element along at least a portion of its length. A helically coiled element may be disposed at a distal end of the flexible tubular member, the flexible tubular member optionally further comprising a flexible tube coupled to the helically coiled element that is disposed proximal to the coiled element.

In this aspect, the flexible tubular member may comprise a flexible tube.

In this aspect, the implant subassembly may have a proximal end that is configured to be locked to the handle subassembly.

In this aspect, the implant subassembly may have a proximal end sized and configured such that the implant subassembly proximal end is adapted to be advanced through a handle subassembly elongate tubular member and into a handle of the handle subassembly. The implant subassembly proximal end may be configured to be locked in place relative to the handle. The implant subassembly proximal end may include a detachable component and a static component that are coupled together in a first state when the proximal end is locked in place relative to the handle, the detachable component secured to the first coupling member, and the static component secured to the second coupling member, the detachable component may be adapted to be separated from the static component in a second state to release the implant from the coupling mechanism. In this aspect, a static component may be locked in place relative to the handle, the detachable component optionally adapted to be detached from the static component by moving the detachable component proximally relative to the static component, wherein proximal movement of the detachable component optionally moves the first coupling member proximally to release the implant from the coupling mechanism.

In this aspect, an implant subassembly proximal end may be configured such that the first coupling member can be locked in place relative to the handle. The first coupling member is optionally axially movable relative to the second coupling member upon application of an axial force at an interface between an implant subassembly detachable component and an implant subassembly static component.

In this aspect, an implant subassembly proximal end optionally includes a region having a smaller outer dimension than axially adjacent regions, the smaller outer dimension adapting the proximal end to be locked in place relative to the handle. A region is optionally a first region, the implant subassembly proximal end optionally including a second region axially spaced from the first region and having a smaller outer dimension than axially adjacent regions, the smaller outer dimension of the second region further adapting the proximal end to be locked in place relative to the handle. A detachable component optionally includes the first region and a static component optionally includes the second region, the detachable component secured to the first coupling member, the detachable component and the first coupling member adapted to be moved proximally relative to the static component to release the implant from the coupling mechanism.

In this aspect, an implant subassembly proximal end optionally has first and second depressions therein that are configured to be locked in place relative to the handle of the handle subassembly.

In this aspect, the implant subassembly may further comprise an implant subassembly packaging in which a handle used to deliver the implant is optionally not disposed.

In this aspect, a distal end of the implant subassembly optionally has at least one surface configured and sized to be coupled to a proximal end of a delivery catheter. A distal end of the implant subassembly is optionally a distal end of the cartridge.

One aspect of this disclosure is an implant and delivery system adapted to be coupled during a medical procedure that delivers the implant. The system may include an implant subassembly that includes a cartridge and an implant disposed in a collapsed state within the cartridge, the implant having an implant proximal end, an implant elongate flexible tubular member with a distal end adjacent the implant proximal end, and an implant coupling mechanism including first and second coupling members that extend through the implant flexible tubular member, the first and second coupling members coupled to the implant proximal end in a first state and positioned and configured to release the implant proximal end when in a second state. The system may also include a handle subassembly including a handle comprising an outer housing and a handle actuator, a handle elongate tubular member in operable communication with the handle actuator, wherein actuation of the handle actuator causes axial movement of the elongate tubular member, the handle elongate tubular member having a lumen sized to receive therein the proximal end of the implant subassembly, the implant flexible tubular member, and the first and second coupling members, and the handle further comprising an implant subassembly locking mechanism that is positioned and adapted to be actuated by a user to lock a proximal end of the implant subassembly within the handle after the implant subassembly is moved proximally through the handle elongate tubular member and into the handle during a medical procedure to implant the implant.

In this aspect, the handle assembly optionally includes an implant subassembly stopper at least partially disposed within the handle, the implant subassembly stopper positioned within the handle to stop the proximal end of the implant subassembly from further proximal movement within the handle. An implant subassembly stopper is optionally positioned to stop the proximal end of the implant subassembly from further proximal movement at a position that axially aligns one or more locking members of the implant subassembly locking mechanism with one or more corresponding lock features on the proximal end of the implant subassembly.

In this aspect, the implant subassembly locking mechanism optionally includes an actuator and one or more locking elements, the actuator configured to be actuated by a user to cause the one or more locking elements to interface with the proximal end of the implant subassembly and lock the proximal end of the implant subassembly in place. Actuation of the actuator optionally causes one of the one or more locking elements to move radially inward and interface with an outer surface of the proximal end of the implant subassembly and lock the proximal end of the implant subassembly in place. An outer surface is optionally an outer surface of a detachable component of the implant subassembly. A detachable component is optionally secured to the first coupling member. Actuation of an actuator optionally causes a second locking element to move radially inward and interface with a second outer surface of the proximal end of the implant subassembly to further lock the proximal end of the implant subassembly in place. A second outer surface is optionally an outer surface of a static component of the implant subassembly.

In this aspect, the handle assembly optionally includes a second handle actuator, the second handle actuator in operable communication with the implant subassembly locking mechanism such that when the second handle actuator is actuated, a first portion of the implant subassembly locking mechanism is moved. The first portion may include a proximal locking member. A second locking member may not be moved with a first locking member upon actuation of the second handle actuator.

In this aspect, the handle assembly may further include a second handle actuator, the second handle actuator optionally in operable communication with the first coupling member such that when the second handle actuator is actuated, the first coupling member is moved axially to release the implant from the coupling mechanism.

In this aspect, the implant subassembly is optionally packaged in a first packaging and the handle subassembly is packaged in a second packaging different than the first packaging.

In this aspect, the implant elongate flexible tubular member optionally has a distal end and the handle elongate tubular member has a distal end, wherein the distal end of the implant elongate flexible tubular member is optionally more flexible than the distal end of the handle elongate tubular member.

In this aspect, the implant elongate tubular member optionally comprises a coiled element.

One aspect of the disclosure is a method of assembling an implant subassembly and a handle subassembly. The method may optionally include removing an implant subassembly from a first packaging, the implant subassembly comprising a proximal end and an implant in a collapsed state within a cartridge; removing a handle subassembly from a second packaging, the handle subassembly including a handle and an elongate handle tubular member in operable communication with the handle actuator, wherein actuation of the handle actuator causes axial movement of the elongate handle tubular member, advancing the proximal end of the implant subassembly into a distal end of the elongate handle tubular member, through the elongate handle tubular member and into a handle of the handle subassembly; and locking the proximal end of the implant subassembly in place relative to the handle subassembly.

In this aspect, advancing the proximal end of the implant subassembly into the handle optionally comprises advancing the proximal end of the implant subassembly until it engages with an implant subassembly stopper in the handle.

In this aspect, locking a proximal end of the implant subassembly relative to the handle subassembly optionally comprises moving a locking element into a locked position relative to the proximal end of the implant subassembly.

In this aspect, moving a locking element into a locked position relative to a proximal end of the implant subassembly optionally comprises moving the locking element into engagement with a detachable component of the implant subassembly, the detachable component secured to a first coupling member of the implant subassembly, the first coupling member part of a coupling mechanism that is coupled to the implant in a first state, the first coupling member moveable relative to the implant to release the implant.

In this aspect, locking the proximal end of the implant subassembly relative to the handle subassembly may comprise moving a second locking element into engagement with a proximal end of the implant subassembly. Moving a second locking element optionally comprises moving the second locking element into engagement with a static component of the implant subassembly, the static component optionally coupled to a second coupling member of the coupling mechanism, the second locking element and the second coupling member not movable axially after being locked in place relative to the handle.

In this aspect, locking the proximal end of the implant subassembly optionally comprises actuating, optionally by depressing, a handle lock actuator.

In this aspect, the method may comprise delivering the implant to a target location, and releasing the implant, the releasing step optionally comprising actuating a handle actuator to move a detachable component of the proximal end of the implant subassembly, the proximal end of the implant subassembly secured to an implant coupling member.

In this aspect, an advancing step optionally further comprises advancing an elongate implant tubular member through the elongate handle tubular member, the elongate implant tubular member having a distal end that is adjacent an implant proximal end.

One aspect of the disclosure is a method of assembling an implant subassembly and a handle subassembly. The method may include advancing a proximal end of an implant subassembly into a distal end of an elongate handle tubular member of a handle subassembly, through the elongate handle tubular member and into a handle of the handle subassembly; and locking the proximal end of the implant subassembly in place relative to the handle subassembly. The implant subassembly may further comprise an implant and a cartridge, the implant in a collapsed state within the cartridge during the advancing step. The handle subassembly may further comprise a handle actuator in operable communication with the elongate handle tubular member such that actuation of the handle actuator causes axial movement of the elongate handle tubular member.

In this aspect, advancing the proximal end of the implant subassembly into the handle may include advancing the proximal end of the implant subassembly until it engages with an implant subassembly stopper in the handle.

In this aspect, locking the proximal end of the implant subassembly relative to the handle subassembly may comprise moving a locking element into a locked position relative to the proximal end of the implant subassembly. Moving a locking element into a locked position relative to the proximal end of the implant subassembly may comprise moving the locking element into engagement with a detachable component of the implant subassembly, the detachable component secured to a first coupling member of the implant subassembly, the first coupling member part of a coupling mechanism that is coupled to the implant in a first state, the first coupling member moveable relative to the implant to release the implant.

In this aspect, locking the proximal end of the implant subassembly relative to the handle subassembly may comprise moving a second locking element into engagement with the proximal end of the implant subassembly. Moving a second locking element may comprise moving the second locking element into engagement with a static component of the implant subassembly, the static component optionally coupled to a second coupling member of the coupling mechanism, the second locking element and the second coupling member not movable axially after being locked in place relative to the handle.

In this aspect, locking the proximal end of the implant subassembly may comprise actuating (optionally depressing) a handle lock actuator.

In this aspect, the method may further comprise delivering the implant to a target location, and releasing the implant, the releasing step optionally comprising actuating a handle actuator to move a detachable component of the proximal end of the implant subassembly, the proximal end of the implant subassembly secured to an implant coupling member.

In this aspect, the advancing step may further comprise advancing an elongate implant tubular member through the elongate handle tubular member, the elongate implant tubular member optionally having a distal end that is adjacent an implant proximal end.

BRIEF DESCRIPTION OF THE DRAWINGS

FIG. 5 illustrates an exemplary coupling mechanism shown coupled to an exemplary proximal end of an exemplary implant.

FIG. 11 illustrates an exemplary delivery catheter.

FIG. 12 illustrates an exemplary system coupled to a proximal end of an exemplary delivery catheter.

DETAILED DESCRIPTION

The disclosure herein is related to medical implant packaging and delivery system solutions that can avoid having to package many complete systems that include external handles coupled to medical implants. The disclosure herein is related to modular pre-loaded implant subassemblies that can be packaged separately from a handle subassembly, which provides the ability to use any one of many separately packaged modular pre-loaded implants with a common handle. This eliminates a need to have implants pre-coupled to the delivery system and packaged therewith, thus potentially eliminating a great deal of packaging and space needed to place the packaged implants during the medical procedure.

One aspect of this disclosure describes implant and delivery systems that include an implant subassembly adapted to be coupled to a handle subassembly during a medical procedure. The implant subassembly may be packaged separately from the handle subassembly.

Figure 1:
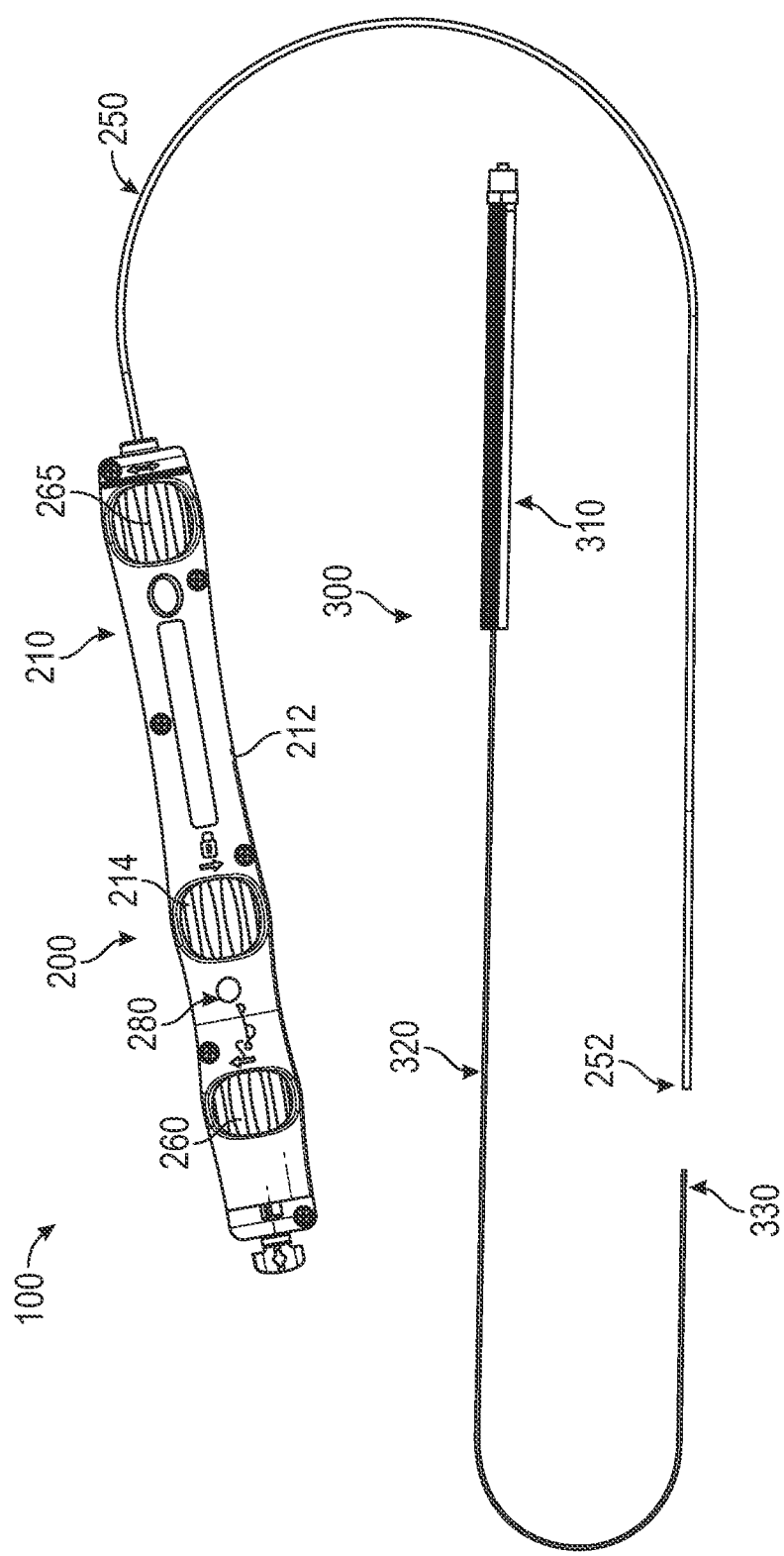
FIG. 1 illustrates an exemplary system that includes a handle assembly and an implant subassembly.

FIG. 1 illustrates an exemplary implant and delivery system 100 in an uncoupled state. System 100 includes an implant subassembly 300 that is adapted to be coupled to handle subassembly 200 during a medical procedure. FIG. 1 illustrates the two subassemblies after removal from separate packaging but before they are coupled.

Implant subassembly 300 includes cartridge 310 and an implant (not visible) disposed within cartridge 310, optionally in a collapsed state within the cartridge. The implant disposed in the cartridge includes an implant proximal end, which is also not visible in FIG. 1. Implant subassembly 300 also includes an elongate flexible tubular member 320 with a distal end (not visible in FIG. 1) that is coupled to the implant proximal end. Implant subassembly includes proximal end 330. Elongate flexible tubular member 320 may be configured as a tubular member or may be configured as a helically coiled member.

In this example, handle subassembly 200 includes a handle 210 and an elongate tubular member 250 extending within the handle 210 and also distally from handle 210. Handle 210 also includes an outer housing or shell 212 and a handle actuator 214. Actuator 214 is adapted to be actuated by a user and is in operable communication with the elongate tubular member 250, wherein actuation of the handle actuator 214 causes axial movement of elongate tubular member 250, which is described in more detail below. Tubular member 250 has a distal end 252 and a lumen extending therethrough that is in communication with distal end 252. Distal end 252 and the lumen within tubular member 250 are sized and configured to receive therein proximal end 330 of implant subassembly 300, implant flexible tubular member 320, as well as implant first and second coupling members, which are described below.

Figure 2:
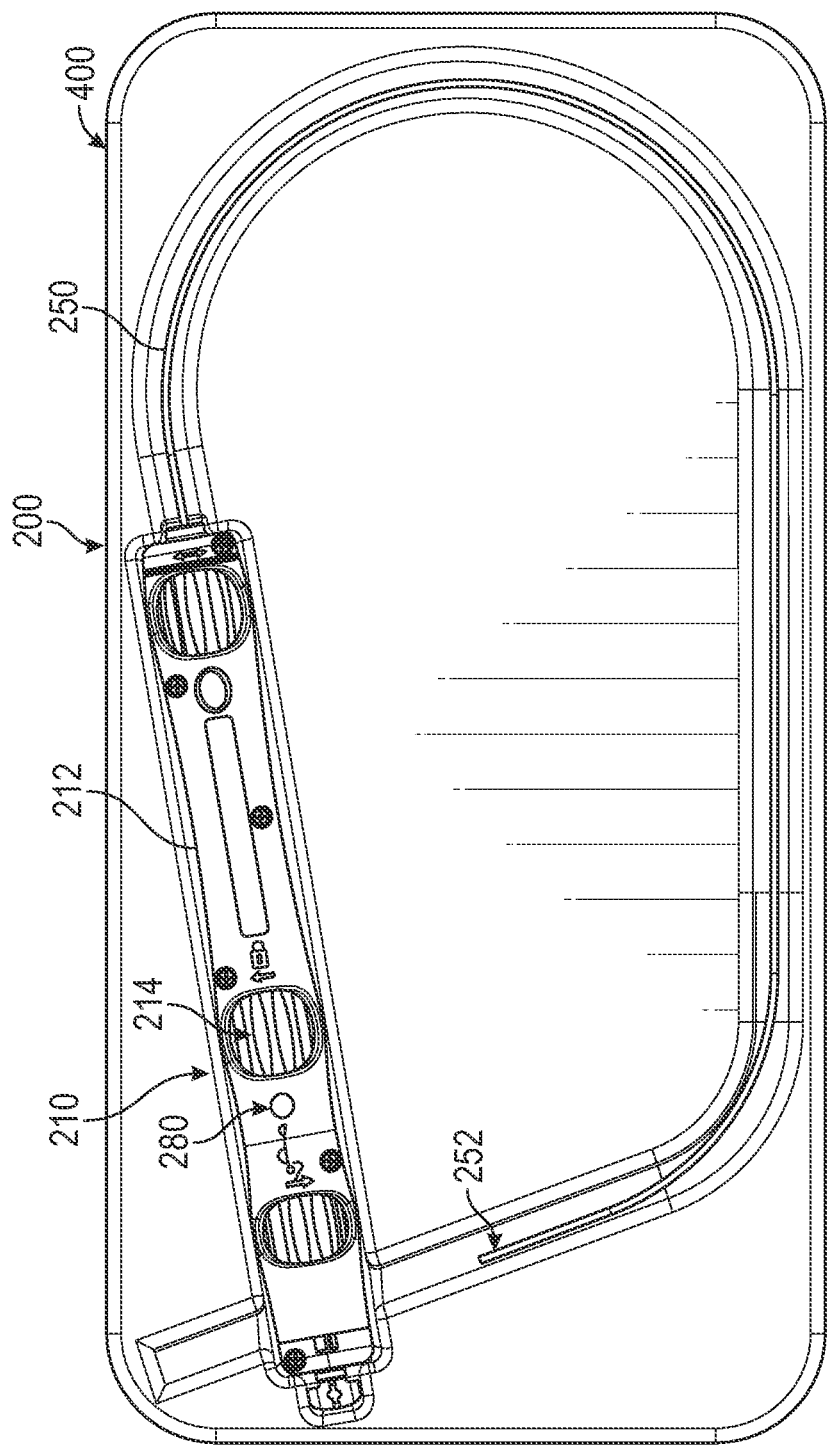
FIG. 2 illustrates an exemplary handle subassembly in an exemplary handle subassembly packaging.

FIG. 2 illustrates an exemplary packaging 400 for handle subassembly 200, with a recess formed therein for handle 210 and a recess formed therein to receive elongate tubular member 250 member therein. One or more sections of elongate tubular member 250 are adapted to be stored in a non-linear configuration, as shown, and are configured to revert to a linear configuration when removed from packaging 400. One or more sections of elongate tubular member 250 may also be stored in linear configurations, as shown. Elongate tubular member 250 may be stored in other configurations not shown, any of which may have some degree of non-linearity in one or more sections along its length in the packaging. Packaging elongate tubular member 250 in a configuration that is not completely straight also reduces the length dimension of the package needed for the handle subassembly.

Handle elongate tubular member 250 may, in some merely exemplary embodiments, be made of a flexible tubular material that allows for some degree of bending for packaging. The material of the elongate tubular member 250 may allow for both flexibility (for packaging), as well as have the necessary stiffness for avoiding buckling and for implant actuation.

Figure 3:
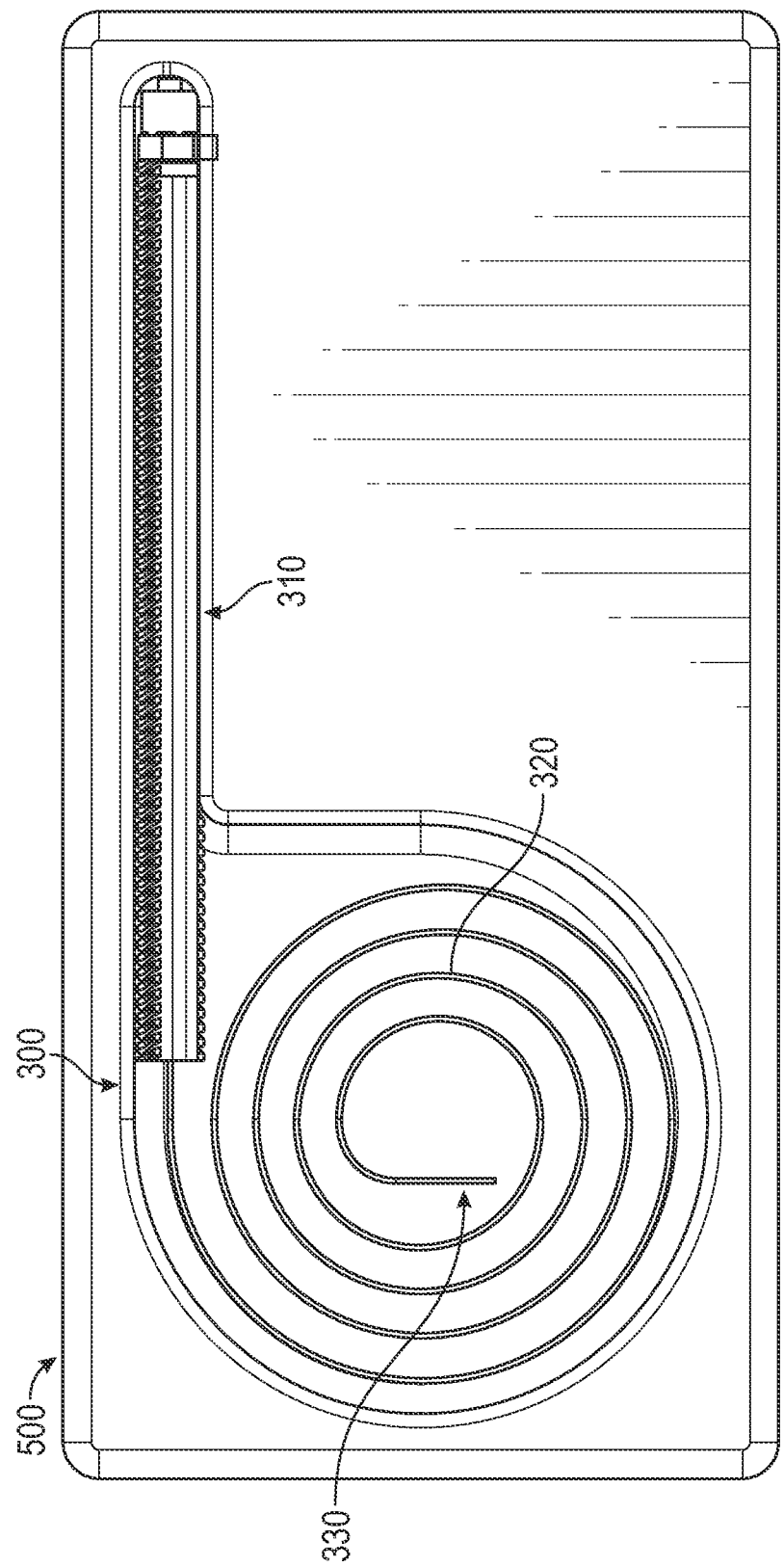
FIG. 3 illustrates an exemplary implant subassembly in an exemplary implant subassembly packaging.

FIG. 3 illustrates an exemplary packaging 500 for an individual implant subassembly. Tubular member 320 may optionally be configured in a non-linear configuration as shown to reduce the packaging size. The flexibility of tubular member 320 as shown may allow for individual modular pre-loaded implants to be disposed in much smaller packaging than if assembled to the handle and packaged together.

Figure 4A:
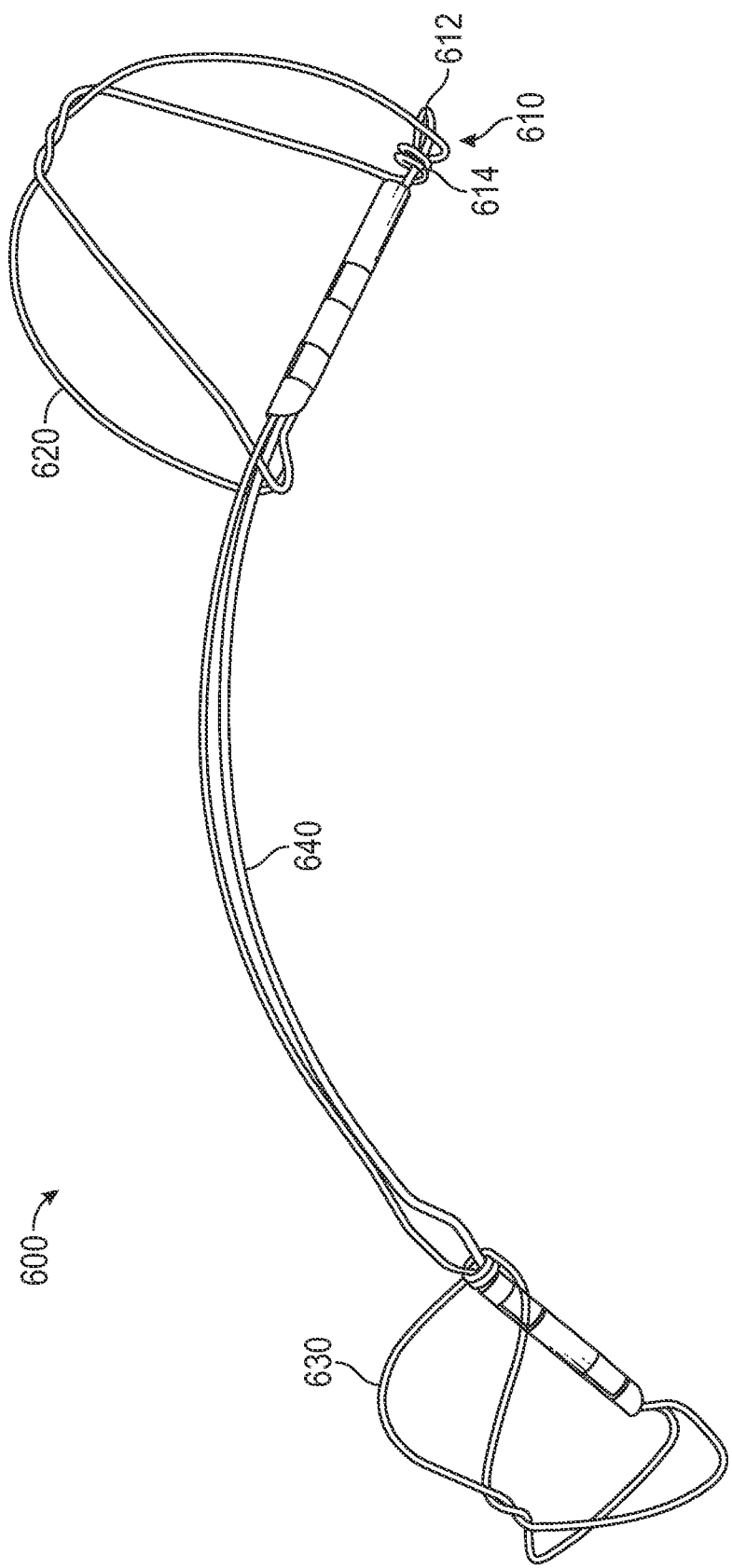
FIG. 4A illustrates an exemplary implant.
Figure 4B:
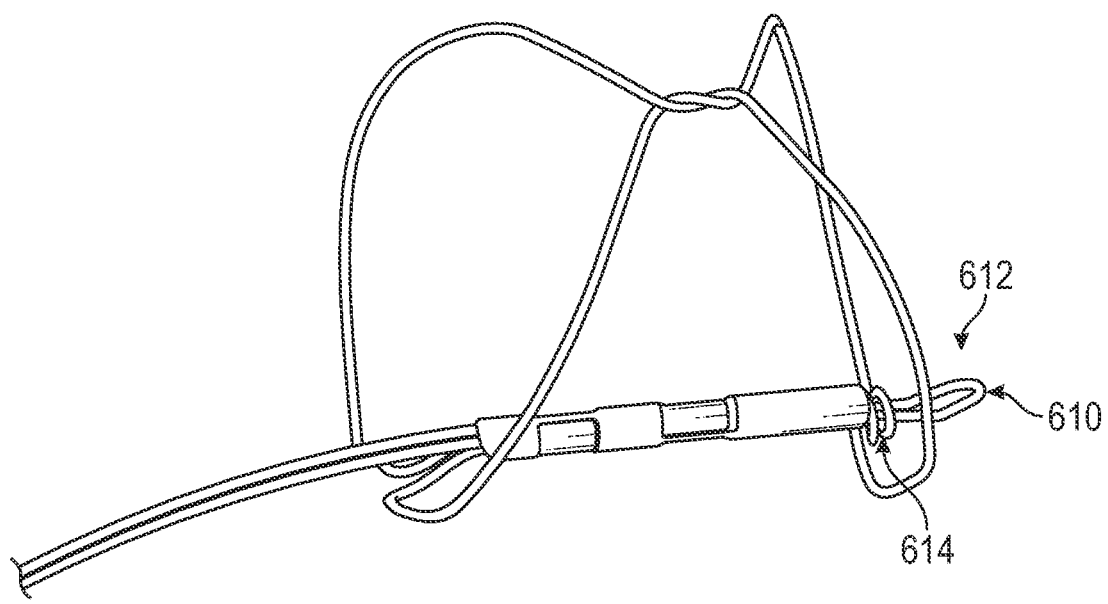
FIG. 4B illustrates an exemplary proximal region of the exemplary implant in FIG. 4A.

FIGS. 4A and 4B illustrates a merely exemplary implant 600 that is shown already decoupled from a handle subassembly, and is shown in an exemplary expanded, implanted configuration. Implant 600 is an example of an implant that may be packaged as a modular pre-loaded implant according to the disclosure herein. It is understood that a wide variety of other implants may benefit from incorporating the modular pre-loaded implant concepts herein, and that implant 600 is merely an illustrative implant. FIG. 4B illustrates proximal region 610 in more detail, including proximal anchor eyelet 614 and looped element 612, which may be referred to herein as an arrowhead.

FIG. 5 illustrates an exemplary coupling mechanism 332 which is shown coupled to proximal end 610 of implant 600. In this example, coupling mechanism retains implant 600 until implant 600 is ready to be fully released and implanted in a patient. The coupling mechanism in this example includes first coupling member 340 and second coupling member 350. First and second coupling members 340 and 350 are shown coupled to the implant proximal end 610 in a first state, and are also adapted to release the implant proximal end 610 when in a second state, which is described in more detail below. Generally, in the first coupled state, second coupling member 350 has a looped distal end configuration that extends into an opening created by arrowhead 612. First coupling member 340 (which may be referred to herein as a lock wire) extends through second coupling member 350 and through arrowhead 612, wherein the arrangement between the first coupling member, the second coupling member, and the implant proximal end in this state prevents the release of the implant. To release implant 600, first coupling member 340 is retracted proximally beyond arrowhead 612, which release the proximal end of the implant, and which is described in more detail below.

Figure 6:
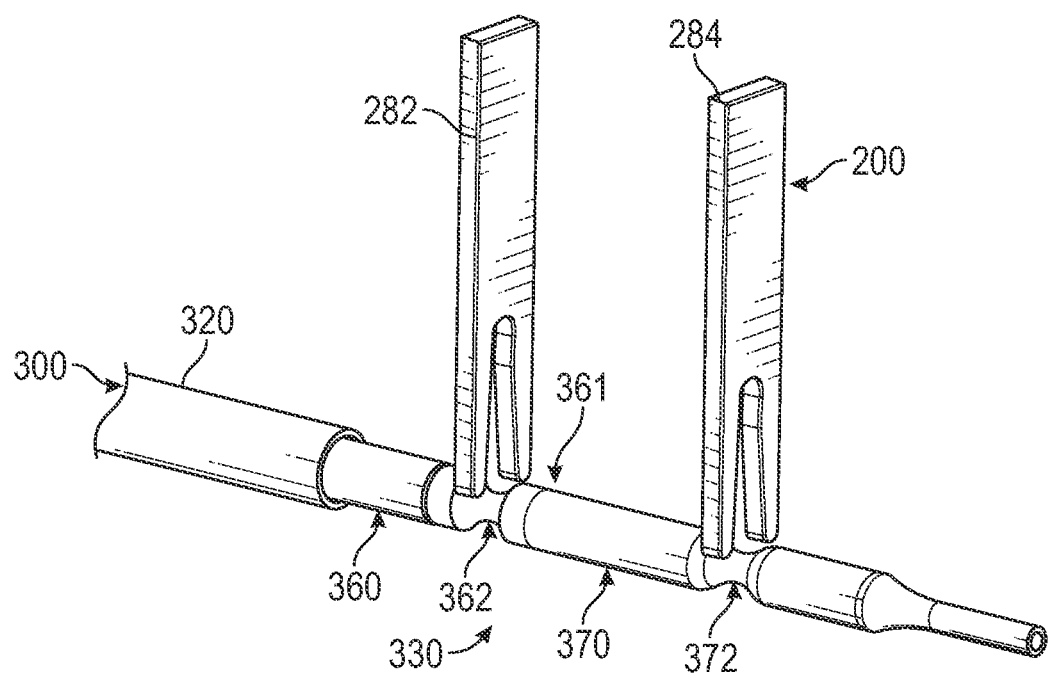
FIG. 6 illustrates a proximal region of an exemplary implant subassembly and a portion of an exemplary handle subassembly.
Figure 7:
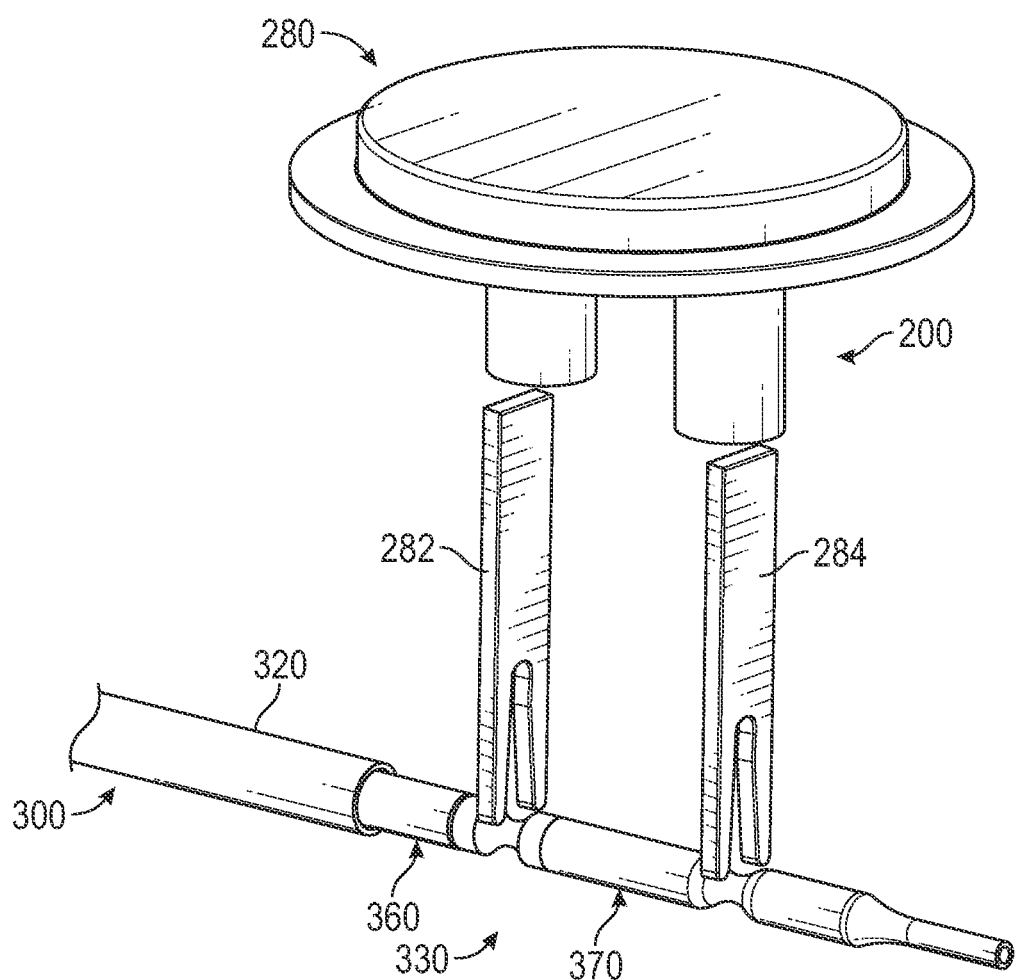
FIG. 7 illustrates a proximal region of an exemplary implant subassembly and a portion of an exemplary handle subassembly.
Figure 8:
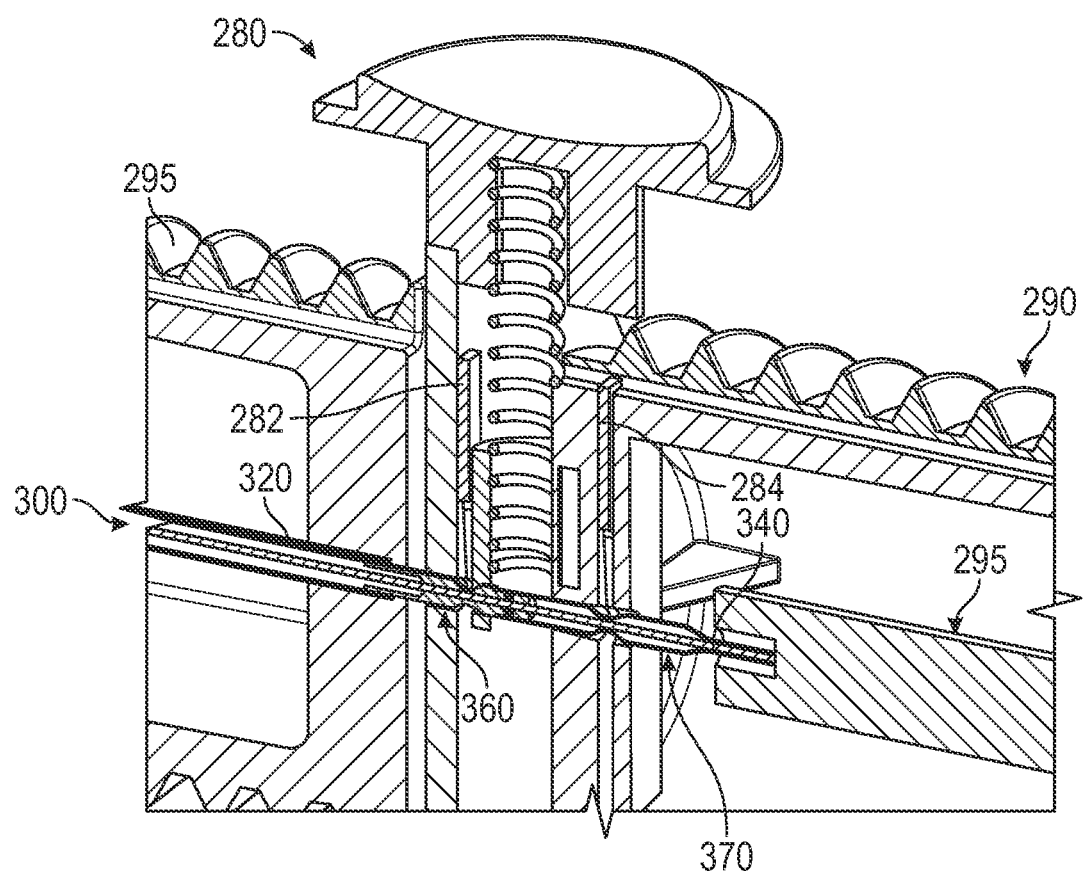
FIG. 8 illustrates a proximal region of an exemplary implant subassembly disposed within a portion of an exemplary handle subassembly.

First and second coupling members 340 and 350 extend through flexible tubular member 320 as shown in FIG. 5, and are coupled to respective implant subassembly components at the proximal end of the implant subassembly, details of which are shown in FIGS. 6-8.

After one of the medical implants has been selected from the available implants, the selected modular pre-loaded implant subassembly is removed from its individual packaging, such as packaging 500 shown in FIG. 3. The handle subassembly, which may be adapted to be used with any of the implant subassemblies, is also removed from its separate packaging. The proximal end 330 of the implant subassembly 300 is then front loaded into the distal end 252 of the handle subassembly. The flexible tubular member 320, in which first and second coupling members are disposed, is advanced proximally through elongate member 250 and into handle 210.

One aspect of this disclosure is a separate modular pre-loaded implant subassembly that includes a proximal end that can be advanced into and locked in place within the delivery handle during the medical procedure by medical personnel, which provides the packaging advantages set forth herein. FIG. 5 illustrates an elongate and flexible tubular member 320, as well as first and second coupling members 340 and 350, both of which extend through a lumen within tubular member 320. FIGS. 6-8 illustrate a merely exemplary implementation of proximal end 330 of the implant subassembly that is sized and configured to be advanced into a handle subassembly and locked in place during a medical procedure. In this exemplary and particular example, first coupling member 340 (an example of which is shown in FIG. 5) is coupled to detachable component 370 of the proximal end 330 of the implant subassembly 300. Second coupling member 350 (an example of which is shown in FIG. 5) is coupled to static component 360 of the proximal end 330 of the implant subassembly 300. Preferably the second coupling member 350 is secured to the static component 360 under tension. Second coupling member 350 may be secured or coupled to static component 360 in a variety of ways, such as by one or more of bonding, adhesive(s), or other common coupling techniques. In this exemplary embodiment, the second coupling member 350 serves to secure the first coupling member 340 in such a way as to lock the implant to the delivery system until the first coupling member 340 is pulled proximally to release the implant. FIG. 8 illustrates a perspective sectional view showing first coupling member 340 extending through static component 360 and through detachable component 370, and coupled to detachable component 370. First coupling member 340 is secured to detachable component 370 such that when detachable component 370 is moved proximally, first coupling member 340 is also moved proximally (and relative to static component 360 which does not move axially), which releases the implant from the delivery system.

One aspect of this disclosure is a handle subassembly that includes an implant subassembly locking mechanism that is positioned and adapted to lock a proximal end of the implant subassembly within the handle after the implant subassembly is moved proximally through the handle elongate tubular member and into the handle during a medical procedure to deploy the implant. The implant subassembly locking mechanism may be adapted to be actuated by a user to lock the proximal end of the implant subassembly within the handle, an example of which is described with respect to FIGS. 6-8.

In some exemplary embodiments, the handle subassembly may further include an implant subassembly stopper at least partially disposed within the handle, the implant subassembly stopper positioned within the handle to interface with and stop a proximal end of the implant subassembly from further proximal movement, the stopper positioned such that the implant subassembly locking mechanism can be actuated to lock the proximal end of the implant subassembly within the handle. An implant subassembly stopper may provide the advantage of automatically stopping the implant subassembly at a particular location within the handle such that locking may be simple and successfully performed by user actuation of a lock actuator, described in more detail below. FIG. 8 illustrates an exemplary stopper 295, having a distal end positioned and configured to stop the proximal movement of the implant subassembly at a particular location. Any of the stoppers here may also function as safety release member that must be removed from the handle prior to the implant from being released. For example, the stopper and safety release can interact with the handle such that the coupling member 340 cannot physically be retracted proximally until the stopper/safety member is removed from the handle.

In the exemplary embodiment in FIGS. 6-8, the implant subassembly locking mechanism of the handle subassembly includes lock actuator 280 (also see FIG. 1) that is positioned and adapted relative to handle housing 212 to be actuated by a user to lock the proximal end 330 of the implant subassembly within the handle after the implant subassembly is moved proximally through the handle elongate tubular member and into the handle during a medical procedure to implant the implant. The implant subassembly locking mechanism includes first and second locking elements 282 and 284, which are positioned and configured to be actuated radially inward toward the proximal end 330 of the implant subassembly upon actuation of lock actuator 280 (e.g., depressing a handle button). The first and second locking elements 282 and 284 are positioned and configured to, upon actuation of lock actuator 280, move radially inward and interface with static component 360 and detachable component 370, respectively, to lock the proximal end 330 in place relative to the handle.

In this merely exemplary and particular embodiment, locking elements 282 and 284 are configured as clips and each have surfaces that are configured to lockingly interface with outer surfaces of axially spaced regions 362 and 372 on static and detachable components 360 and 370, respectively. In this non-limiting example, axially spaced regions 362 and 372 each have smaller outer dimensions than axially adjacent regions, the smaller outer dimension adapting the regions 362 and 372 to be locked in place relative to the handle. In this embodiment the regions 362 and 372 may be considered to have depressions therein in the outer surfaces that are configured to be locked in place relative to the handle of the handle subassembly. In an alternative embodiment, the lock actuator may not be needed by having both locking elements 282 and 284 spring loaded and configured differently so that fork 282 may slide over region 372 as the implant subassembly is being introduced into the handle subassembly and then fork 284 could then drop into region 372. Alternative arrangements are contemplated. For example, locking elements could be configured as modulated irises to close radially into regions 362 and 372, where modulation could be triggered automatically by proximal end 330 of implant subassembly passing through the handle, where no lock actuator may be necessary. In other embodiments, a boss could be provided to drop into slots provided in static component 360 and detachable component 370. The boss may be cammed or not.

As set forth above, detachable component 370, to which first coupling member 340 is secured, is adapted to be moved proximally within the handle relative to static component 360 to cause first coupling member 340 to be retracted and release the implant. Detachable component 370 is coupled to region 372 such that they move proximally together. Static component 360 is coupled to region 362 such that they remain static together when detachable component is pulled proximally. Separation location 361 is shown in FIG. 6 where detachable component 370 separates from static component 360. In one embodiment, this is accomplished by actuating handle release actuator 260 (see FIG. 1), which is in operative communication with detachable component 370 via locking element 284. As shown in FIG. 8, locking element 284 is secured within threaded member 290, which is in threaded engagement with handle release actuator 260. When handle release actuator 260 (not shown in FIG. 8) is actuated (e.g., rotated), threaded member 290 is moved axially due to the threaded relationship and the handle release actuator 260 is axially fixed in place (but can rotate). Axial movement of threaded member 290 causes locking element 284 to move axially as well. Locking element 284 is locked to detachable component 370, which is coupled to first coupling member 340. This exemplary arrangement causes the proximal movement of first coupling member 340, thereby releasing the implant. Actuation of handle release actuator 260 thereby causes the release of the implant. This disclosure thereby describes a modular pre-loaded implant that can be locked in place to the handle during the medical procedure, yet an implant coupling member can be moved relative to the handle to facilitate the release of the implant when desired.

Lock element 282 is not disposed within threaded member 290, and thus does not move proximally with lock element 284 when handle release actuator 260 is actuated. This configuration is thus an example of how to prevent a static member from moving when a detachable member needs to be moved to release the implant.

The disclosure that follows illustrates exemplary method steps that may be performed during coupling and delivery of an implant. Some method steps that follow are described above. Not all method steps that follow need necessarily be performed, and one or more steps may in fact be illustrative and/or optional.

One aspect of this disclosure is a method of assembling an implant subassembly and a handle subassembly. The method may include removing an implant subassembly (e.g., 300) from a first packaging (e.g., 500), the implant subassembly comprising a proximal end and an implant in a collapsed state within a cartridge. The method may also include removing a handle subassembly (e.g., 200) from a second packaging (e.g., 400), the handle subassembly including a handle and an elongate handle tubular member in operable communication with a handle actuator (e.g., 214), wherein actuation of the handle actuator causes axial movement of the elongate handle tubular member. The method may further include advancing the proximal end of the implant subassembly into a distal end of the elongate handle tubular member, through the elongate handle tubular member and into a handle of the handle subassembly. The method may further include locking the proximal end of the implant subassembly in place relative to the handle subassembly.

Figure 9:
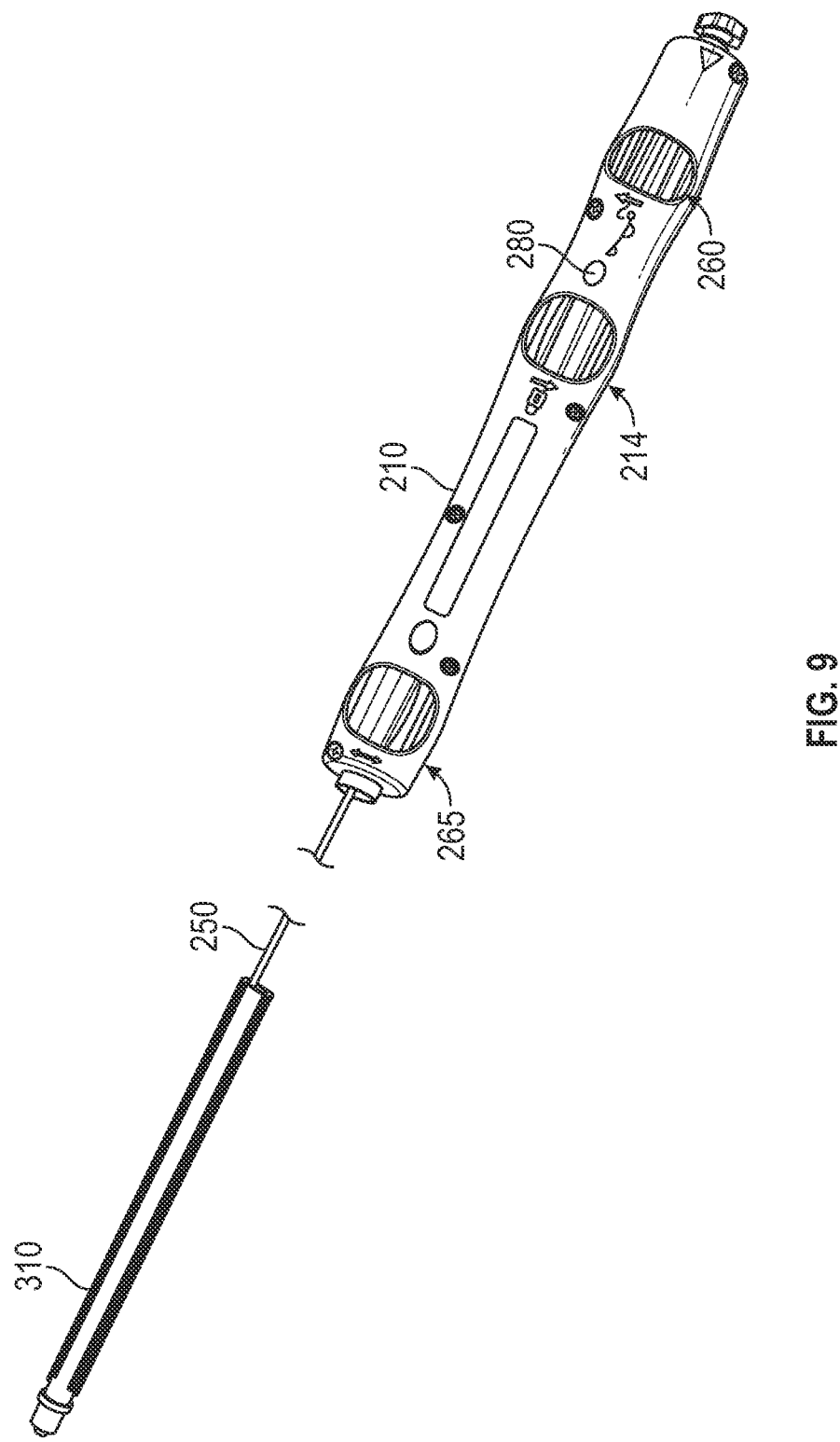
FIG. 9 illustrates an exemplary system including an exemplary handle subassembly and an exemplary implant subassembly.

Once the implant subassembly is locked in place relative to the handle, the locked system is in the configuration shown in FIG. 9, with implant elongate tubular member 320 (not visible) within handle elongate tubular member 250 and within handle 210. The distal end of handle elongate tubular member 250 is just proximal to the implant (not visible) in the cartridge. The handle elongate tubular member 250 may be much longer than is shown in FIG. 9, with the two curved lines indicating a length of the tubular member 250 that is not shown.

Figure 10:
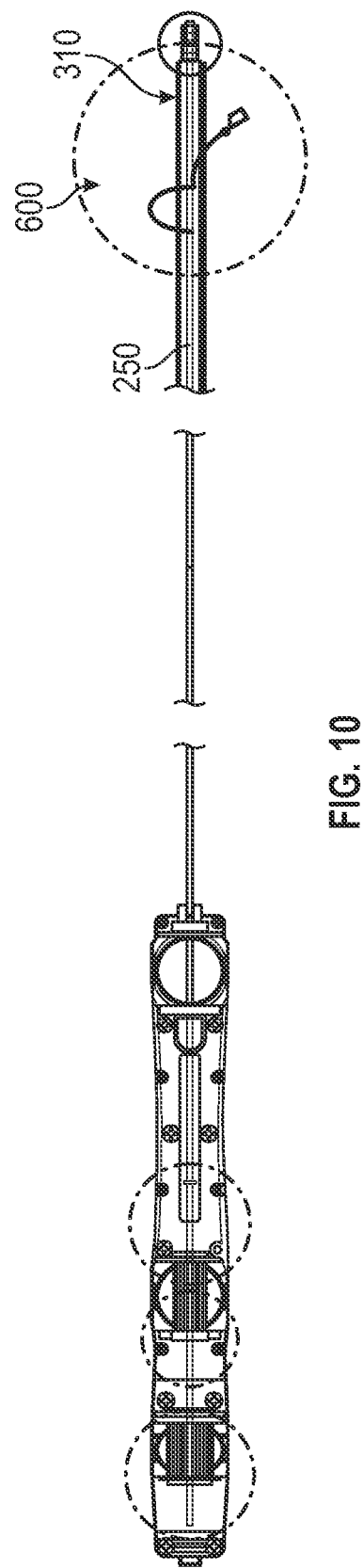
FIG. 10 is illustrative of an exemplary system including an exemplary handle subassembly and an exemplary implant subassembly.

FIG. 10 illustrates by way of example only a relative position of an implant 600 inside cartridge 310, even though FIG. 10 illustrates the implant 600 in a deployed and optionally curved configuration. Any of the implants herein may be non-expandable implants, but may still be pre-loaded within a cartridge or other elongate housing. The term cartridge herein may thus be replaced globally with a more generic term such as elongate housing with a lumen therein, and it may be rigid.

In some exemplary embodiments, the distal end of the cartridge may then be coupled to a proximal end 902 of a delivery catheter 900, an example of which is shown in FIG. 11. Distal end 904 of the catheter is also shown. In some exemplary embodiments, a delivery catheter 900 may have a length from 50 cm to 90 cm, such as from 60 cm to 80 cm.

FIG. 12 illustrates an exemplary luer lock connection between the cartridge and the delivery catheter (after advancement of the handle assembly and implant through the delivery catheter).

After coupling the cartridge to the delivery catheter 900, the handle assembly 200, handle elongate tubular member 250, implant elongate tubular member 320, and the implant are advanced distally relative to the cartridge until the handle comes into contact with the cartridge, as shown in FIG. 12. The cartridge outer threads are configured to mate with internal threads on delivery catheter control actuator 265, such that once mated, actuation of actuator 265 controls axial movement of the cartridge and the delivery catheter, which is now coupled to the cartridge. Axial movement of the cartridge and the delivery catheter allows for unsheathing and sheathing of the implant as may be needed, with the implant now positioned at the distal end and within the delivery catheter. After the implant is deployed from the delivery catheter, which may occur by moving the delivery catheter relative to the implant, the implant may be released. Removal of a safety member (which may also be a stopper as described herein), such as is shown at the proximal end of handle in FIG. 9, may occur to allow the implant release. As is described in more detail above, the release actuator 260 may be actuated to cause locking member 284 to move proximally, which causes the proximal movement of detachable component 370 and first coupling member 340, thereby releasing the implant. The delivery system may then be removed.

As set forth above, advancing the proximal end of the implant subassembly into the handle may also comprise advancing the proximal end of the implant subassembly until it engages with an implant subassembly stopper (e.g., 295) in the handle.

Locking the proximal end of the implant subassembly relative to the handle subassembly may include moving a locking element (e.g., 284) into a locked position relative to the proximal end of the implant subassembly. The locking element may be moved into engagement with a detachable component (e.g., 370) of the implant subassembly, the detachable component secured to a first coupling member (e.g., 340) of the implant subassembly, the first coupling member part of a coupling mechanism that is coupled to the implant (e.g., 600) in a first state, the first coupling member moveable relative to the implant to release the implant. Locking the proximal end of the implant subassembly relative to the handle subassembly may further comprise moving a second locking element (e.g., 282) into engagement with the proximal end of the implant subassembly, and optionally into engagement with a static component (e.g., 360) of the implant subassembly. The static component may be coupled to a second coupling member (e.g., 350) of the coupling mechanism, wherein the second locking element and the second coupling member not movable axially after being locked in place relative to the handle.

Locking the proximal end of the implant subassembly may comprises actuating (optionally depressing) a handle lock actuator (e.g., 280), although other types of actuators may be implemented.

At a time that is subsequent to locking the proximal end of the implant subassembly, any of the methods herein may further comprise delivering the implant to a target location, and releasing the implant. The releasing step may comprise actuating a release handle actuator (e.g., 260) to cause the movement of a detachable component (e.g., 370) of the proximal end of the implant subassembly, the proximal end of the implant subassembly secured to an implant coupling member (e.g., 340).

The entire delivery system may then be removed from the patient, leaving the implant implanted at the target location.

What is claimed is:

1. An implant and delivery system adapted to be coupled during a medical procedure that delivers the implant, comprising:
   an implant subassembly including:
      a cartridge and an implant disposed in a collapsed state within the cartridge, the implant having an implant proximal end,
      an implant elongate flexible tubular member with a distal end adjacent the implant proximal end, and
      an implant coupling mechanism including first and second coupling members that extend through the implant flexible tubular member, the first and second coupling members coupled to the implant proximal end in a first state and positioned and configured to release the implant proximal end when in a second state; and
   a handle subassembly including:
      a handle comprising an outer housing and a handle actuator,
      a handle elongate tubular member in operable communication with the handle actuator, wherein actuation of the handle actuator causes axial movement of the elongate tubular member,
      the handle elongate tubular member having a lumen sized to receive therein the proximal end of the implant subassembly, the implant flexible tubular member, and the first and second coupling members, and
      the handle further comprising an implant subassembly locking mechanism that is positioned and adapted to lock a proximal end of the implant subassembly within the handle after the implant subassembly is moved proximally through the handle elongate tubular member and into the handle during a medical procedure to implant the implant.

2. The system of claim 1, wherein the handle assembly includes an implant subassembly stopper at least partially disposed within the handle, the implant subassembly stopper positioned within the handle to stop the proximal end of the implant subassembly from further proximal movement within the handle.

3. The system of claim 2, wherein the implant subassembly stopper is positioned to stop the proximal end of the implant subassembly from further proximal movement at a position that axially aligns one or more locking members of the implant subassembly locking mechanism with one or more corresponding lock features on the proximal end of the implant subassembly.

4. The system of claim 1, wherein the implant subassembly locking mechanism includes an actuator and one or more locking elements, the actuator configured to be actuated by a user to cause the one or more locking elements to interface with the proximal end of the implant subassembly and lock the proximal end of the implant subassembly in place.

5. The system of claim 4, wherein actuation of the actuator causes one of the one or more locking elements to move radially inward and interface with an outer surface of the proximal end of the implant subassembly and lock the proximal end of the implant subassembly in place.

6. The system of claim 5, wherein the outer surface is an outer surface of a detachable component of the implant subassembly.

7. The system of claim 6, wherein the detachable component is secured to the first coupling member.

8. The system of claim 6, wherein actuation of the actuator causes a second locking element to move radially inward and interface with a second outer surface of the proximal end of the implant subassembly to further lock the proximal end of the implant subassembly in place.

9. The system of claim 8, wherein the second outer surface is an outer surface of a static component of the implant subassembly.

10. The system of claim 1, wherein the handle assembly includes a second handle actuator, the second handle actuator in operable communication with the implant subassembly locking mechanism such that when the second handle actuator is actuated, a first portion of the implant subassembly locking mechanism is moved.

11. The system of claim 10, wherein the first portion includes a proximal locking member.

12. The system of claim 10, wherein a second locking member is not moved with the first locking member upon actuation of the second handle actuator.

13. The system of claim 1, wherein the handle assembly includes a second handle actuator, the second handle actuator in operable communication with the first coupling member such that when the second handle actuator is actuated, the first coupling member is moved axially to release the implant from the coupling mechanism.

14. The system of claim 1, wherein the implant subassembly is packaged in a first packaging and the handle subassembly is packaged in a second packaging different than the first packaging.

15. The system of claim 1, wherein the implant elongate flexible tubular member has a distal end and the handle elongate tubular member has a distal end, wherein the distal end of the implant elongate flexible tubular member is more flexible than the distal end of the handle elongate tubular member.

16. The system of claim 1, wherein the implant elongate tubular member comprises a helically coiled element.

17. The system of claim 1, wherein the helically coiled element is disposed at a distal end of the implant flexible tubular member, the implant flexible tubular member further comprising a flexible tube coupled to the coiled element that is disposed proximal to the helically coiled element.

18. The system of claim 1, wherein the implant flexible tubular member comprises a flexible tube.

19. The system of claim 1, wherein the implant subassembly comprises a proximal end that includes a detachable component and a static component that are coupled together in a first state when the proximal end is secured in place relative to the handle, the detachable component secured to the first coupling member, and the static component secured to the second coupling member, the detachable component adapted to be separated from the static component in a second state to release the implant from the coupling mechanism.

20. The system of claim 19, wherein the second coupling member is attached to the static component under tension.

* * * * *